（12）United States Patent
Dunne et al.

(10) Patent No.: US 7,841,338 B2
(45) Date of Patent: Nov. 30, 2010

(54) DISPENSING DEVICE

(75) Inventors: Stephen Terence Dunne, Stowmarket (GB); Herbert Wachtel, Ingelheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 864 days.

(21) Appl. No.: 11/735,250

(22) Filed: Apr. 13, 2007

(65) Prior Publication Data

US 2007/0240714 A1 Oct. 18, 2007

(30) Foreign Application Priority Data

Apr. 13, 2006 (EP) ................... 06007887
Jun. 6, 2006 (EP) ................... 06011613

(51) Int. Cl.
*A61M 1/04* (2006.01)
(52) U.S. Cl. .............. 128/203.12; 128/200.18
(58) Field of Classification Search ............ 128/203.12, 128/203.15, 203.24, 203.23, 203.28, 200.18
See application file for complete search history.

(56) References Cited

U.S. PATENT DOCUMENTS

| | | | |
|---|---|---|---|
| 5,469,843 A | 11/1995 | Hodson | |
| 5,724,959 A * | 3/1998 | McAughey et al. .... | 128/203.15 |
| 5,918,594 A | 7/1999 | Asking et al. | |
| 6,488,648 B1 | 12/2002 | Matsugi et al. | |
| 7,617,822 B2 * | 11/2009 | De Boer et al. ........ | 128/203.15 |
| 2005/0263151 A1 | 12/2005 | Hochrainer et al. | |
| 2006/0213514 A1 | 9/2006 | Price et al. | |

FOREIGN PATENT DOCUMENTS

| | | |
|---|---|---|
| CA | 2 297 174 A1 | 2/1999 |
| GB | 2248400 A | 4/1992 |
| GB | 2 375 310 A | 11/2002 |
| WO | 92/12799 A1 | 8/1992 |
| WO | 93/18811 A1 | 9/1993 |
| WO | 99/07340 A1 | 2/1999 |
| WO | 99/58180 A1 | 11/1999 |
| WO | 2005/002654 A2 | 1/2005 |

* cited by examiner

*Primary Examiner*—Steven O Douglas
(74) *Attorney, Agent, or Firm*—Roberts Mlotkowski Safran & Cole, P.C.

(57) ABSTRACT

A dispensing device for dispensing powder as a spray is disclosed. The dispensing device comprises a duct through which the powder is dispensable by gas pressure for de-agglomerating the powder. The duct is angled by at least about 90 degrees at a diversion portion and/or diverted into two opposite directions at a fork portion so that the powder is impacted on to or sheared by a solid surface for powder de-agglomeration.

19 Claims, 7 Drawing Sheets

DISPENSING DEVICE

BACKGROUND OF THE INVENTION

The present invention relates to a dispensing device for dispensing powder as a spray.

FIELD OF THE INVENTION

Powder drugs delivered through dispensing devices, in particular, inhalers, are intended to optimally target specific sites in the pulmonary system. These sites include the nasal passages, the throat, and various locations within the lungs, such as the bronchi, bronchioles and alveolar regions. The ability to deliver drugs to a target area depends inter alia on the aerodynamic sizes of the particles. As currently believed to be understood, particles having an aerodynamic diameter of less than 2 µm are considered to be potentially optimal for deposition in the alveolar region of the lung. Particles that have an aerodynamic diameter of between 2 and approximately 5 µm may be more suitable for delivery to the bronchiole or bronchi regions. Particles with an aerodynamic size range greater than 6 µm, and more preferably, 10 µm, are typically suitable for delivery to the laryngeal region, throat or nasal passages.

In most cases, it is desired to achieve a high inhalable fraction and high delivery efficiency, i.e., the fraction that reaches the desired region, in particular, in the lung. This depends on various factors, in particular, on the characteristics of the generated spray plume, such as propagation velocity of the plume, particle size and its distribution, fraction of small particles, fraction of gas and the like. In the present invention, the desired spray plume characteristics include, preferably, a small particle size, a high fraction of drug particles with a diameter of 6 µm less, a low propagation velocity, a long duration of spray generation and/or possible inhalation, and/or a low amount of gas volume required for dispensing a certain amount of powder.

In particular, the present invention is concerned with dry powder inhalers for the delivery of drugs to the lungs. Many dry powder inhalers are on the market or have been proposed. There are two main types, namely the passive ones and the active ones. In passive inhalers all the energy required for de-agglomerating the powder and transferring the powder to the lungs is provided by the breathing of a user or patient. In active inhalers there is an additional source of energy to help to de-agglomerate the powder.

Most powder inhalers are of the passive type where the powder is inhaled by the patient without the aid of an additional energy source. The problem with passive inhalers is that the inhalable fraction, or the proportion of powder that actually enters the lungs, is largely dependant on the breathing of the patient. The de-agglomeration of the powder and hence the inhalable fraction is a function of the flow rate of inhaled air through the device, and therefore, varies greatly from patient to patient.

Dry powder inhalers are subdivided into single dose devices and multi-dose inhalers. Multi-dose inhalers are further subdivided into pre-metered types where the doses are stored individually and into metering inhalers where the powder dose is metered in the device.

Multi dose pre-metered inhalers have the advantage that the single doses are metered under strict factory conditions and the powder can quite easily be isolated from the atmosphere. In many applications, the active drug powder is mixed with a carrier such as lactose which tends to absorb humidity from the atmosphere which makes it stick together and difficult to de-agglomerate.

The present invention relates, in particular, to an active, gas powered, pre-metered multi-dose or single-dose dispensing device for dispensing powder containing or consisting of a drug, such as a dry powder inhaler.

International Patent Application Publication WO 92/12799 A1, which forms the starting point of the present invention, discloses a pre-metered dispensing device for transforming a flow of fluid into a spray of fine particle size, wherein an annular flow is caused through a stem filled with powder with a velocity gradient within that flow sufficient to cause sheer forces between components of the flow to break the flow up into a spray. An angled duct leads from the outlet of the stem to an outlet orifice in a spray head. However, the known device is not optimal for de-agglomerating the powder and for generating a slow spray plume with the desired characteristics.

SUMMARY OF THE INVENTION

A primary object of the present invention is to provide an improved dispensing device which achieves better de-agglomeration of the powder.

A main aspect of the present invention is that the duct is angled by at least about 90 degrees at a diversion portion and/or is diverted into two at least substantially opposite directions at a fork portion so that the powder is impacted on to and/or sheared by a solid surface (impaction or deflection surface) for powder de-agglomeration. The impaction of the powder particles on the surface or wall results in a surprisingly good de-agglomeration of the powder particles. An explanation may be that very high shear forces are generated by the impaction or deflection of the powder particles. The use of a diversion portion and/or fork portion has not been recognized in the prior art for the impaction and powder de-agglomeration according to the present invention.

According to a preferred embodiment, the duct comprises multiple diversion portions and/or fork portions in order to further enhance powder de-agglomeration. In particular, the duct is designed such that the powder is impacted on to and/or sheared by multiple solid surfaces or surface portions—in particular, of the duct wall in the regions of the diversion portions and/or fork portions—for powder de-agglomeration.

Preferably, the duct is bent and/or angled alternately in opposite directions. This enables a compact design with very good powder de-agglomeration.

According to a preferred embodiment, the duct is a capillary. This leads to a very effective impaction of the powder particles to the solid surface and/or to high shear forces and, thus, to good powder de-agglomeration. Preferably the duct is located at a mouthpiece entrance and/or exits into a mouthpiece with no flow restrictions after the duct.

Preferably, the duct comprises a flat cross section. The powder is forced through the duct by pressurized gas to de-agglomerate the powder and to generate a spray including fine powder particles. The ratio of the largest side to the smallest side of the flat cross section of the duct is at least 2.0. Surprisingly, a much better de-agglomeration and finer particles can be achieved, in particular, with a lower amount of gas for a given volume or mass of powder, than by a circular or quasi circular duct. This effect may be explained in that the flat cross section provides a larger perimeter for a given cross sectional area than a non-flat cross section. This larger perimeter results in a larger duct surface that is in contact with the gas and powder so that better de-agglomeration can be achieved due to higher sheer forces without changing the cross sectional area (hydraulic diameter), i.e., without changing the flow resistance or mass flow significantly.

Preferably, the ratio of the largest side to the smallest side of the flat cross section is from 3 to 50, most preferably, about 5 to 30. Thus, a high output of powder with good de-agglomeration as a spray with small powder particle size can be achieved by a comparatively low gas pressure, low gas volume, and low gas flow rate. The dispensing device produces a plume of de-agglomerated dry powder with a high inhalable fraction and with the desired spray plume characteristics.

It was found that with fine powders of mean particles of fewer than 5 μm a substantially rectangular duct of typically 75 μm by 1500 μm works well. With powders of mean particle size above 30 μm a duct of typically 200 μm by 1500 μm works well. The non circular duct should preferably, have a hydraulic diameter of between 20 to 1000 μm depending on the particle size of the powder. It can be made of any material that is drug compatible including plastics or metals. More than one non circular duct may be used in parallel.

The duct preferably, has a length of at least 5 or 10, preferably, between 10 and 60, hydraulic diameters (the hydraulic diameter is defined as the ratio of 4 cross sectional areas over the duct perimeter). For any given pressure the longer the non circular duct the slower is the powder delivery to the patient. ☐ However, if the duct is too long the velocity in the storing/mixing chamber may be reduced to an extent that the mixing chamber is not emptied.

In particular, it is possible to force the powder through the duct by a gas pressure of less than 300 kPa to de-agglomerate the powder and to generate the spray with fine particle size, so that optimal spray plume characteristics, in particular, a low propagation velocity, can be achieved.

It is advantageous to minimize the exit velocity of the gas and powder in order to minimize powder impaction in the mouth and upper respiratory tract. However, the higher the exit velocity, the better is the powder break up or de-agglomeration. One solution to this is to slow the exit velocity of the gas and powder mixture at the duct exit by using two or more impinging ducts or powder jets, preferably, impinging at an angle of between 30 and 180, preferably, 90 and 150, degrees. This is another aspect of the present invention. In particular, multiple—at least two—powder spray jets are impinged, i.e., hit each other, to slow down the propagation velocity of the spray and/or to de-agglomerate the powder. This supports the desired spray plume characteristics as mentioned above.

Alternatively or additionally, at least one diffuser having an increasing cross section may be used to decelerate the gas and powder flow at the exit of the duct.

Any gas may be used. For instance liquefied gases such as HFA134a and HFA227 may be used. In such a device, the gas is stored in a pressurized canister containing a metering valve with connecting means to the powder reservoir(s). Alternatively a piston cylinder arrangement, a bellows or any other gas pump may be used to pressurize, e.g., atmospheric air. In such a device, the user or patient needs to cock or prime the device prior to use. Further, compressed gas may be used. For single dose devices, a pre-pressurized canister of compressed air may be used.

The volume of gas needed to completely empty a storage chamber (reservoir) and/or mixing chamber depends on the powder volume or mass. For powder masses of 0.1 to 50 mg, gas masses of between 0.2 and 300 mg are required. For instance 5 mg of powder with a mean particle size of 4 μm requires between 10 and 20 $cm^3$ of compressed air at between 100 kPa and 200 kPa with a mass of approximately 20 to 60 mg of air. For coarser powders, less gas volume is needed at lower pressure typically under 100 kPa gauge because less energy is required for de-agglomeration.

The volume of the storage chamber (reservoir) and optional mixing chamber needed to expel all the powder depends on the powder volume or mass. It should preferably, have a volume of between 0.002 and 0.2 $cm^3$ depending on the powder dose. The larger the powder dose, the larger the reservoir/mixing chamber should be. For instance with a powder dose of 5 mg a volume of between 0.015 and 0.03 $cm^3$ is needed for thorough mixing. Preferably, the ratio of the chamber volume (volume of the storage chamber and of the optional mixing chamber) to the powder volume should be between 1.2 and 4.

The reservoir should, preferably, be of cylindrical shape with no sharp edges because sharp edges can attract powder deposits. The gas inlet or inlets should preferably, be positioned so that the gas sweeps all the chamber surfaces to prevent powder accumulating on the surfaces. Preferably, the inlet(s) should be placed near the chamber end furthest from the outlet, i.e., the non circular duct. The relative positions of the entry(s) and outlet in the reservoir and mixing chamber may be arranged in such a way that the gas powder mixture forms turbulent eddies within the chamber to maximize de-agglomeration or that a smooth non-turbulent flow is achieved in the chamber(s).

Preferably, surface areas after the non circular duct are minimized to minimize powder adherence or loss on said surfaces. The invention has the advantage that little or no powder is retained in the device after inhalation and hence the metered and delivered masses are almost the same.

Preferably, the powder is forced through the duct or a nozzle or the like by a comparatively low gas pressure of less than 300 kPa to de-agglomerate the powder and/or to generate the spray. Experiments have shown that such low pressures are sufficient for achieving good de-agglomeration and optimal for achieving a slow spray.

Further aspects, advantages and features of the present invention will be apparent from the following detailed description of preferred embodiments in conjunction with the accompanying drawings.

BRIEF DESCRIPTION OF THE DRAWINGS

FIG. 1a schematic sectional view of a dispensing device according to one embodiment of the present invention;

DETAILED DESCRIPTION OF THE INVENTION

In the drawings, the same reference signs are used for the same or similar components in all embodiments, wherein same or similar characteristics, features or advantages are or can be realized or achieved, even if a repeated discussion is omitted. Further, the features and aspects of the different embodiments can be combined in any desired manner and/or used for other dispensing devices or methods for dispensing powder as desired.

Figure 1:
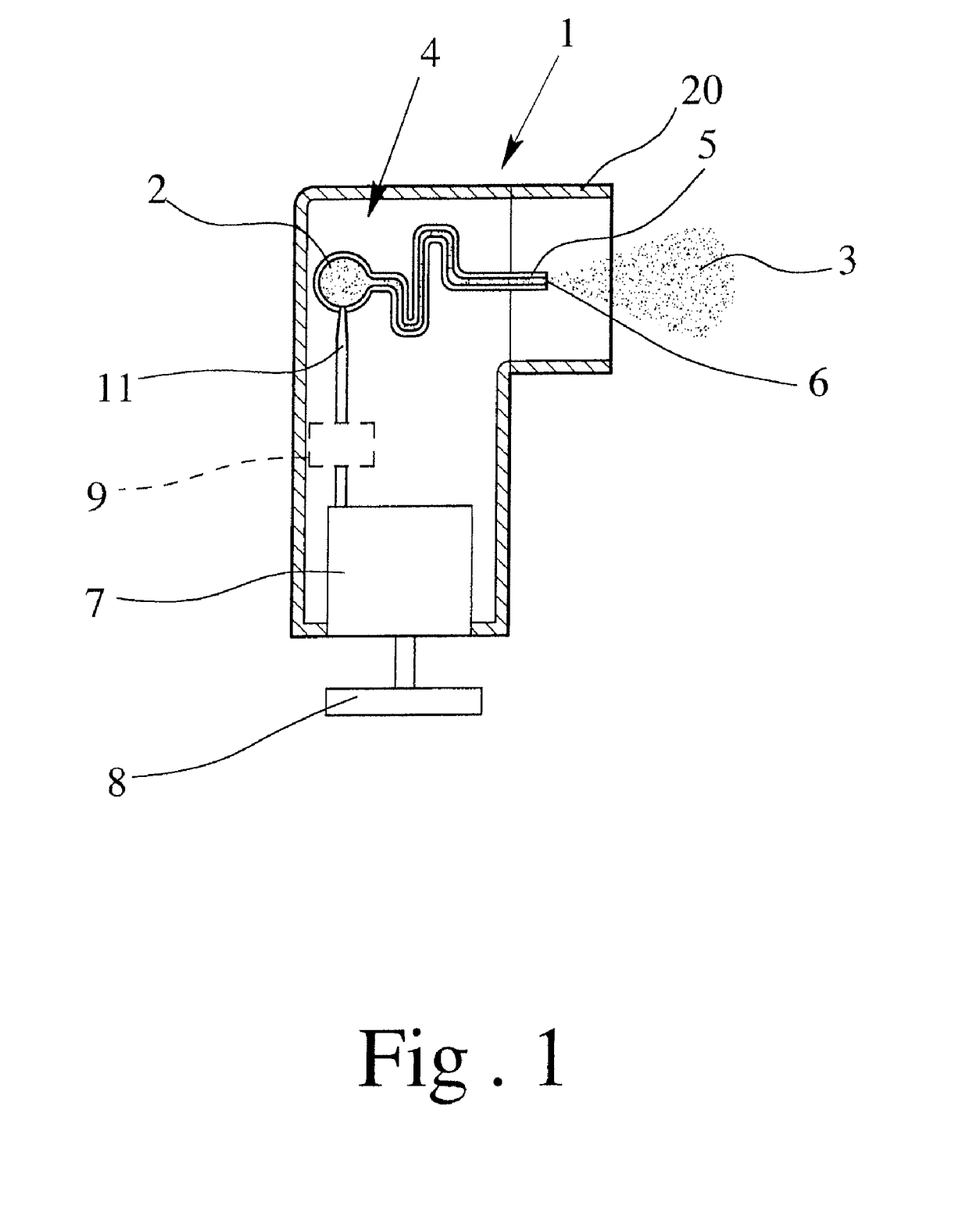

FIG. 1 shows in a schematic cross section—for illustration purposes not to scale—a dispensing device 1 according to the present invention. The dispensing device 1 is an active device, in particular, gas powered. Preferably, the dispensing device 1 is an inhaler, in particular, a dry powder inhaler, for a user or patient (not shown).

The dispensing device 1 is designed to dispense powder 2 which, in particular, contains or consists of at least one drug. The powder 2 may be a pure drug or a mixture of at least two drugs. In addition, the powder 2 may contain at least one other material, in particular, a carrier, such as lactose.

Preferably, the mean diameter of the powder particles is about 2 to 7 μm, in particular, 6 μm or less. This applies in, particular, if the powder 2 does not contain any carrier, such as lactose.

If the powder 2 contains a carrier, such as lactose, and at least one drug, the powder 2 may have a particle size of 20 to 300 μm, in particular, about 30 to 60 μm. However, the de-agglomeration, which will be described later in more detail, may result even in this case in a spray 3 with a smaller particle size, e.g. of about 10 μm or less. In particular, the drug may be separated form the carrier during de-agglomeration so that primarily the drug will be inhaled due to its small particle size of about 2 to 6 μm and the larger carrier will be swallowed when using the dispensing device as an inhaler. Alternatively or additionally, breaking or opening of the carrier is possible during de-agglomeration.

The diameters mentioned above and below may be understood as mass medium aerodynamic diameters and/or may apply to the particle size or a fraction of the particles of the spray 3.

FIG. 1 shows the dispensing device 1 when dispensing the powder 2 as a spray 3 in a very schematic manner. The spray 3 comprises fine (powder) particles, i.e., has fine particle size of preferably, 6 tm or less. In particular, the spray 3 has the desired spray plume characteristics as described above.

The dispensing device 1 is adapted to receive or comprises a storage device 4 for storing the powder 2. The storage device 4 may be integrated into the dispensing device 1 or form part of the dispensing device 1. Alternatively, the storage device 4 may be a separate part, in particular, a container, cartridge, blister or the like that can be inserted or connected with the dispensing device 1 and optionally replaced.

The dispensing device 1 or the storage device 4 preferably, comprises a duct 5 through which the powder 2 is dispensed for de-agglomerating the powder 2 and/or forming the spray 3.

The duct 5 can comprise a nozzle or restriction (not shown) preferably, at the outlet 6.

The dispensing device 1, preferably, uses pressurized gas to force the powder 2 through the duct 5 to de-agglomerate the powder 2 and/or to generate the spray 3 with fine particle size. Preferably, the dispensing device 1 comprises a means for providing pressurized gas, in the present embodiment an air pump 7 which can, preferably, be actuated or operated manually as indicated by handle or actuator 8. In particular, the air pump 7 comprises or is formed by a bellows. However, it could be also a piston-cylinder arrangement. Instead of the air pump 7, the means for providing pressurized gas can be, e.g., a capsule, container or the like containing pressurized or liquefied gas for powering the dispensing device 1, i.e., dispensing the powder 2 as desired.

The air pump 7 may provide a gas pressure of less than 300 kPa, in particular, about 50 to 200 kPa. This is, preferably, sufficient for operating the dispensing device 1. If liquefied gas or a container with pressurized gas is used, the gas pressures might range from 100 kPa to about 700 kPa. Then, the pressure may be reduced or throttled to the preferred pressure range—e.g., by a regulator or control means 9—before supplying the gas to the storage device 4, in particular, its storage chamber 10. The optional regulation or control means 9 is, in particular, a valve, a flow restrictor, a capillary tube or the like, for regulating, throttling and/or controlling the gas flow and/or pressure.

Preferably, all pressure values mentioned in the present description and the claims are gauge pressures, i.e., pressure differences. All pressure values relate to the pressure in a gas storage, such as a container with pressurized or liquefied gas or provided by air pump 7 or relate to the pressures acting in the chamber 10 and/or in the duct 5.

The dispensing device 1 or storage device 4 comprises, preferably, at least one storage chamber 10 containing a single dose of powder 2 that shall be dispensed in a single dispensing operation.

For dispensing, the gas is supplied under pressure to the storage chamber 10 via a gas supply or inlet 11 or the like. Preferably, the inlet 11 is connected or connectable to the means for providing pressurized gas, i.e., in particular, the air pump 7, or to the regulation or control means 9. The gas generates a respective flow in the storage chamber 10 to force essentially all of the powder 2 through the duct 5.

When gas is supplied to the storage chamber 10, the respective dose of powder 2 is dispensed, namely mixed with the gas, forced through the duct 5 and discharged as spray 3 as shown in FIG. 1.

Preferably, the storage device 4, in particular, the chamber 10, is formed with no sharp edges, corners or the like, but have a smooth contour so that the gas can sweep all chamber surfaces to prevent powder 2 accumulating on said surfaces and to ensure or allow complete discharge of the powder 2. In particular, the gas inlet 11 is located opposite to the duct 5 with regard to the axial or outlet direction.

The storage device 4 may comprise only one storage chamber 10 for a single dose, in this case, the storage device 4 is for a single dose only, or may comprise multiple storage cavities 10, and, thus contain multiple doses of powder 2, which can be dispensed subsequently.

The gas supply provided by the dispensing device 1, in particular, air pump 7, can be connected in any suitable manner to the respective storage device 4 or □ storage chamber 1, in particular, to the respective gas inlet 11, preferably, only temporarily when required for a dispensing operation. For example, a piercing element, connecting element or the like can be fluidically connected with gas inlet 11/the respective 
storage chamber 10, in particular, by pushing it through a respective sealing element, diaphragm, membrane, wall portion or the like to open or enable gas supply to the respective storage chamber 10.

Figure 2:
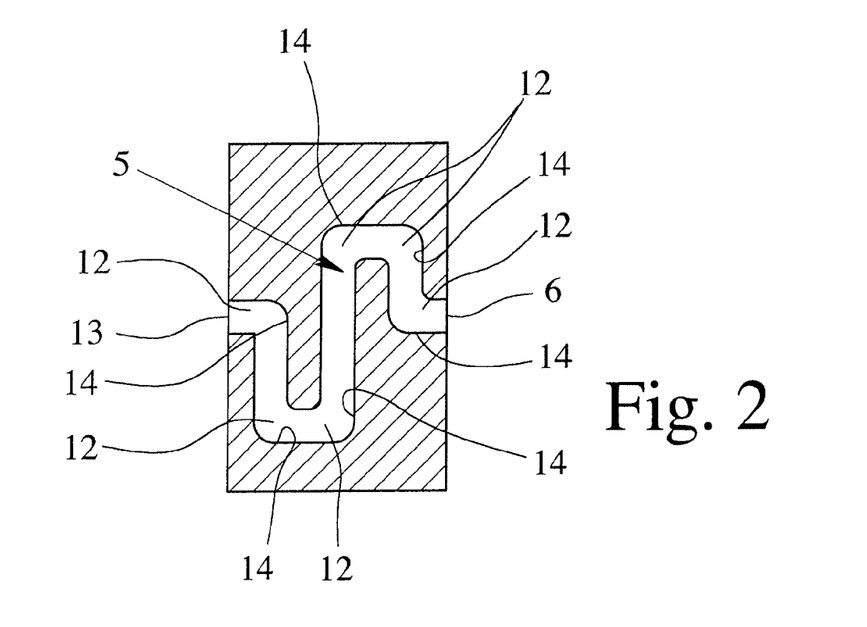
FIG. 2 is a schematic sectional view of a duct of the dispensing device according to FIG. 1.

FIG. 2 shows an enlarged sectional view of FIG. 1, in particular, of the duct design of the dispensing device 1 according to FIG. 1. Here, the duct 5 is angled at least once by at least about 90 degrees at least one diversion portion 12. In this embodiment, the duct comprises multiple diversion portions 12.

The powder 2 entering the duct 5 at its inlet 13 impacts on to and/or is sheared by a solid surface (impaction region) 14 at each diversion portion 12 as indicated in FIG. 2. In the present embodiment, the duct 5 is bent and/or angled, preferably, alternately in opposite directions. In total, the duct 5 comprises six impaction points or regions 14 in the embodiment according to FIGS. 1 & 2. The duct 5 is preferably, angled by about 90 degrees at each diversion portion 12.

Figure 3:
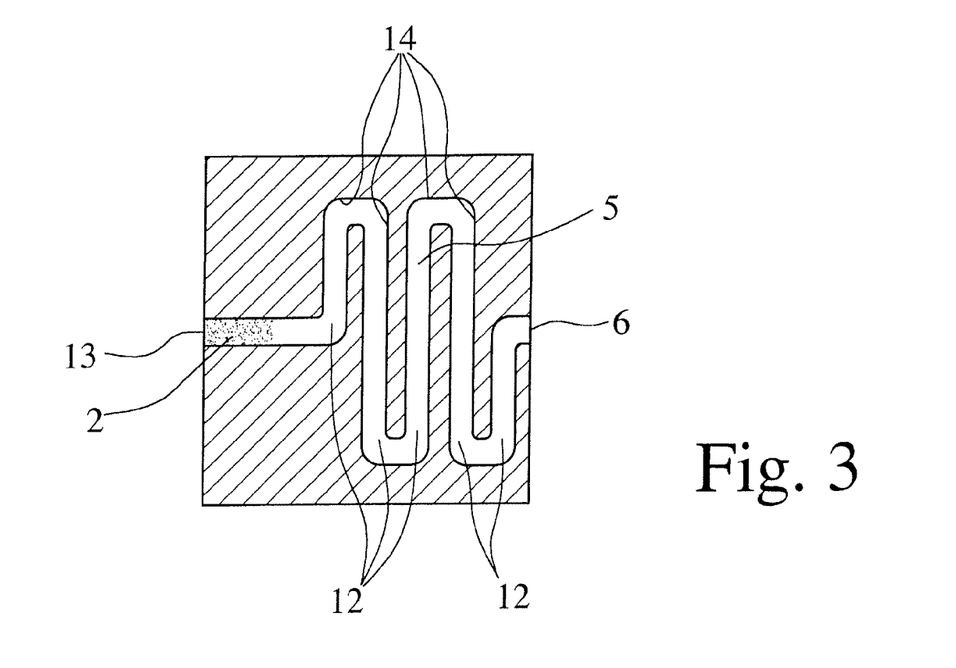
FIG. 3 is a schematic sectional view of a duct of a dispensing device according to another embodiment.
Figure 4:
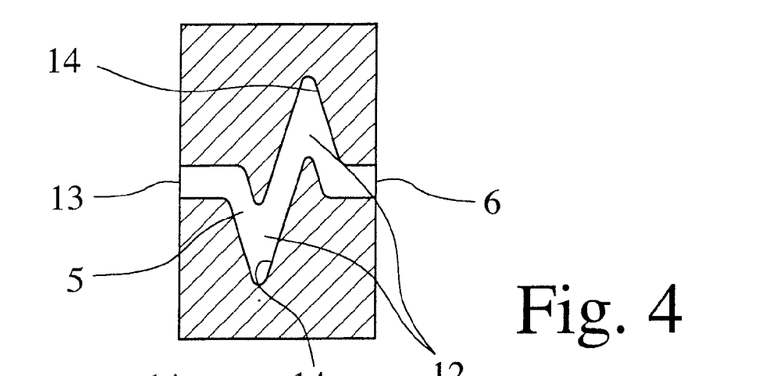
FIG. 4 a schematic sectional view of a duct of a dispensing device according to another embodiment.
Figure 5:
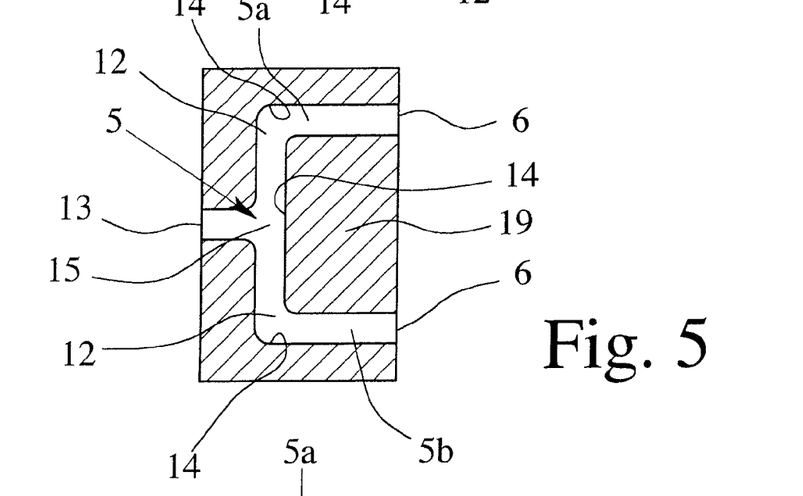
FIG. 5 is a schematic sectional view of a duct of a dispensing device according to another embodiment.

In FIG. 3, the duct 5, preferably, follows a meander-like path. However, other, in particular, folded designs are possible as well.

The de-agglomeration of the powder 2 is preferably, supported or further enhanced by de-agglomeration of the powder 2 by flowing through the preferably, narrow or flat duct 5.

FIG. 3 shows another embodiment of the duct 5 of the dispensing device 1 according to the present invention. Here, the duct 5 is additionally or alternatively used as a reservoir (storage chamber 10) for the powder 2. In this case, the separate or additional storage chamber 10 is not required. Instead, the duct 5 is designed to enable sufficient mixing of the gas with the powder 2, and sufficient de-agglomeration of the powder 2 can be achieved.

Preferably, the first part adjacent to the inlet 13 of the duct 5 forms the storage chamber 10 and/or is filled with the powder 2.

In the embodiment according to FIG. 3, ten diversion portions 12 and, thus, ten impaction points or solid surfaces 14 are formed.

FIG. 4 shows another embodiment with a preferably, zigzag-like or staggering duct configuration. Here, the duct 5 comprises at least two diversion portions 12 where the duct 5 is angled by more than 90 degrees, in particular, more than 135 degrees, preferably, about 150 degrees, resulting in very good powder de-agglomeration.

FIG. 5 shows another embodiment of the duct 5 of the dispensing device 1 according to the present invention. Here, the duct 5 is diverted into two at least substantially opposite directions at a fork portion 15 so that the powder 2 is impacted onto solid surfaces 14 for powder de-agglomeration. In particular, the duct 4 is diverted or branched into two separate branches or ducts 5*a*, 5*b*. Each branch 5*a*, 5*b* comprises a diversion portion 12 as discussed above. In particular, the outlet directions of the two branches 5*a*, 5*b* are essentially parallel in the embodiment according to FIG. 5. However, other duct or outlet configurations are possible as well.

It has to be noted that the two separate branches or ducts 5*a*, 5*b* do not have to be angled 90° relative to the common or supply duct 5 at the fork portion IS, but may be angled only about 50 to 89°, as shown, e.g., in FIG. 6*b*. From the stand point of the invention, this also should be understood as diverting into two at least substantially opposite directions.

In the embodiment according to FIG. 5, three impaction points 14 are formed where the powder particles hit and, thus, de-agglomeration takes place.

FIG. 6*a* shows a similar embodiment. Here, the duct branches 5*a*, 5*b* are angled by more than 90 degrees at the respective diversion portions 12 and, then, bent in opposite directions so that the outlet directions are angled or inclined by each other and/or that a diffuser 16 is formed at or in the outlet 6 of the channel in order to slow the exit velocity.

FIG. 6*b* shows a further embodiment. The duct 5 comprises or diverts into multiple, in particular, more than two, branches and/or diffusers 16. In the present embodiment, the outlet directions are preferably, parallel to each other.

FIG. 6*c* shows a side sectional view of the duct arrangement according to FIG. 6*b*. Preferably, the duct 5 and in particular, the storage chamber 10 are formed by a preferably, rigid base 21 with respective grooves, depressions or the like, covered by a covering 22, in particular, made of foil.

FIG. 6*c* also shows that the storage chamber 10 and the duct 5 are preferably, made by or formed in the same piece of material. This preferred aspect is preferably, realized by all embodiments.

FIG. 7 shows an embodiment in which the branches 5*a*, 5*b* of the duct 5 exit in at least substantially parallel outlet directions similar to the embodiment according to FIG. 5, but closer together.

FIG. 8 shows another, similar embodiment where the two branches 5*a*, 5*b* of the duct 5 are joined at the outlet 6.

FIG. 9 shows a further embodiment similar to FIG. 8, wherein a diffuser 16 is formed at the common outlet 6 of the branches 5*a*, 5*b*.

FIG. 10 shows a further embodiment of the duct 5 of the dispensing device 1 according to the present invention. In this case, the duct 5 is a sequence of two duct arrangements according to FIG. 8. The interconnection 17 forms the outlet of the first duct arrangement and the inlet of the second duct arrangement which are connected in series.

In this embodiment, the duct 5 comprises multiple, namely at least two fork portions 15 where the duct 5 is respectively diverted or split up into two, preferably, directly opposite directions.

FIG. 11 shows, in a schematic sectional view, another duct arrangement with a means for slowing down the velocity which forms a multiple powder jet spray impinging means 18. The means 18 forms multiple—at least two—powder spray jets P which impinge, i.e., hit each other as indicated in FIG. 11. In this embodiment, the duct 5 divides into two sections 5*a*, 5*b* that are designed such that the openings or outlets 6 are inclined relative to each other so that the powder jets P ejecting from the portions 5*a*, 5*b* are inclined relative to each other and impinge. For example, a flow divider 19 or any guiding means can be located in the flow path to form the at least two sections 5*a*, 5*b* of the duct 5 as shown in FIG. 11.

The impinging angle $\alpha$ between the powder jets P is between 30° to 180°, preferably, at least 90°, in particular, about 90° to 150°. The impinging of the powder jets P results in a decrease of the velocity of the spray 3 and/or in a de-agglomeration of the powder 2 and/or in separation of drug particles from a carrier and/or in better focusing of the spray 3. These effects depend on the impinging angle $\alpha$. A larger impinging angle $\alpha$ results in better effects. In contrast to liquid jets, an impinging angle $\alpha$ of 90° and more is possible and preferred. These angles also apply for the following embodiments.

The duct 5 is preferably, at least tangentially connected to the storage chamber 10 in the embodiment shown in FIG. 11. Preferably, the duct 5 is connected to the mixing chamber 10 at one axial end of the cylindrical chamber 14, and the gas inlet 11 is connected to the other axial end of the chamber 10. In particular, the gas inlet 11 is connected also tangentially to the storage chamber 10, such that swirls are generated when entering the gas with a swirl direction supporting discharge of the mixture of gas and powder 2 through the duct 5 which connects tangentially to the rotational direction of the swirl.

Figure 12:
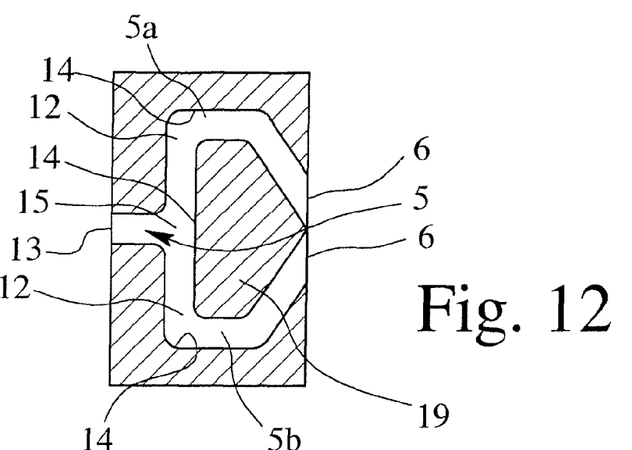
FIG. 12 is a schematic sectional view of a duct of a dispensing device according to another embodiment.

FIG. 12 shows in a schematic sectional view another embodiment of the powder jet impinging means 18. Here, two or more ducts 5 comprise inclined or □ outlet sections 5c which are inclined to each other so that the powder jets P □ ejected from outlet sections 5c impinge with each other.

Figure 11:
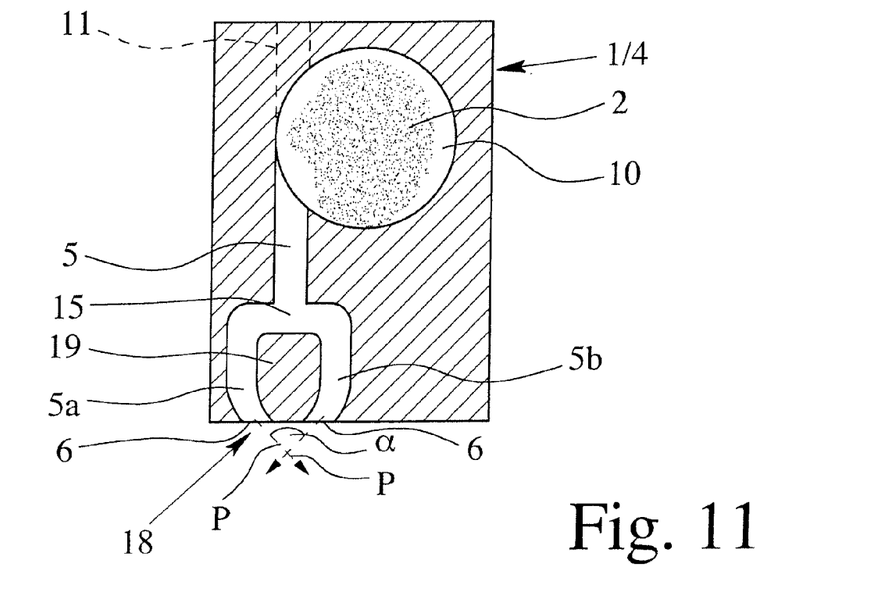
FIG. 11 a schematic sectional view of a duct of a dispensing device according to another embodiment.

The embodiments according to FIG. 11 to 12 are also suitable for impinging more than two powder jets P. For example, it is possible to have similar arrangements in the cross-sectional planes perpendicular to the drawing plane resulting in four outlet directions and powder jets P arranged on the surface of a conus. However, multiple other arrangements with similar effects are possible.

It is also added that the cross sections of the duct sections 5a to 5c are preferably, but not necessarily, rectangular or flat, and can have any suitable cross-sectional shape.

Preferably, the gas inlet 11 or the gas supply comprises a smaller cross-sectional area than the duct 5 or outlet 6 so that the gas flow is determined by the inlet and not by the outlet side, i.e., not by the duct 5 or outlet 6, during dispensing. Then, the mixture of gas and powder 2 is forced by a comparatively low gas pressure through the duct 5 and/or any other suitable outlet such as outlet 6, wherein the gas flow is controlled during this phase at least mainly by the cross section of the gas inlet 11 or any other restriction stream up of gas inlet 11. Due to the comparatively low gas pressure for discharging the powder 2 through duct 5 and/or outlet 6a low discharge velocity and, thus, a low propagation velocity of the spray 3 can be achieved. In addition, the means for slowing down the propagation velocity of the spray 3, in particular, the powder jet impinging means 18, can be used to further decrease the propagation velocity of the spray 3.

Preferably, the spray 3 has a mean velocity (taken 10 cm from the outlet/mouthpiece) of less than 2 m/s, in particular, less than 1 m/s. Preferably, the mean duration of the spray 3 is at least 0.2 or 0.3 s, in particular, about 0.5 to 25 s.

Figures 13A, 13B:
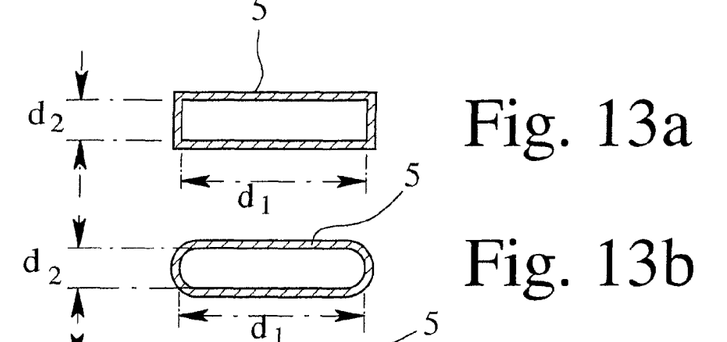
FIGS. 13a-13c are cross-sectional views of ducts with different cross sections.
Figure 13C:
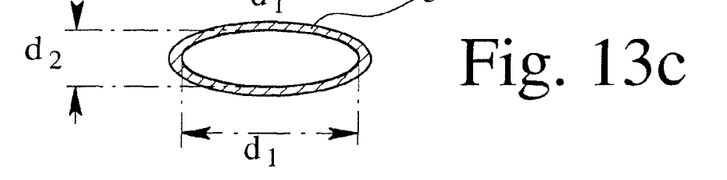

Preferably, the duct 5 has a flat (inner) cross section. FIGS. 13a to 13c show potential cross sections of the duct 5. FIG. 13a shows a substantially rectangular cross section. FIG. 13b shows a flat cross section with two opposite straight sides connected by two curved portions. FIG. 13c shows an oval or elliptical cross section.

Figure 6A:
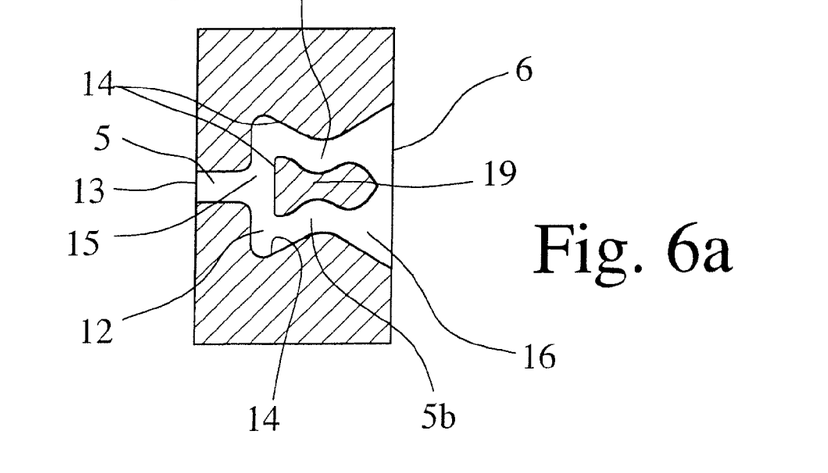
FIG. 6a is a schematic sectional view of a duct of a dispensing device according to another embodiment.
Figure 6B:
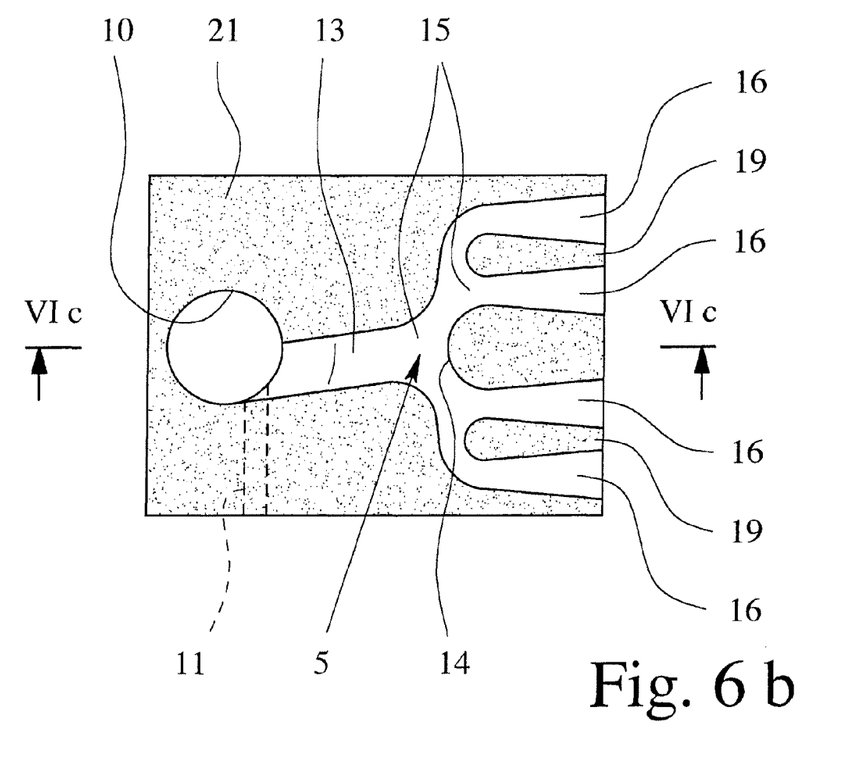
FIG. 6b is a schematic sectional view of a duct of a dispensing device according to another embodiment.
Figure 6C:
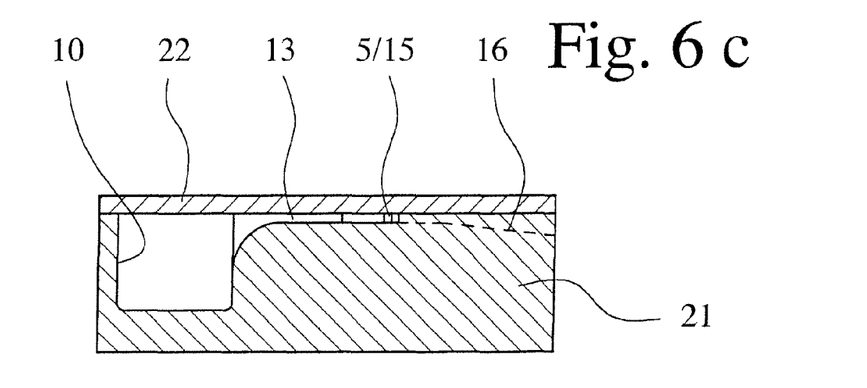
FIG. 6c is sectional view taken along line VIc-Vic of FIG. 6b.
Figure 7:
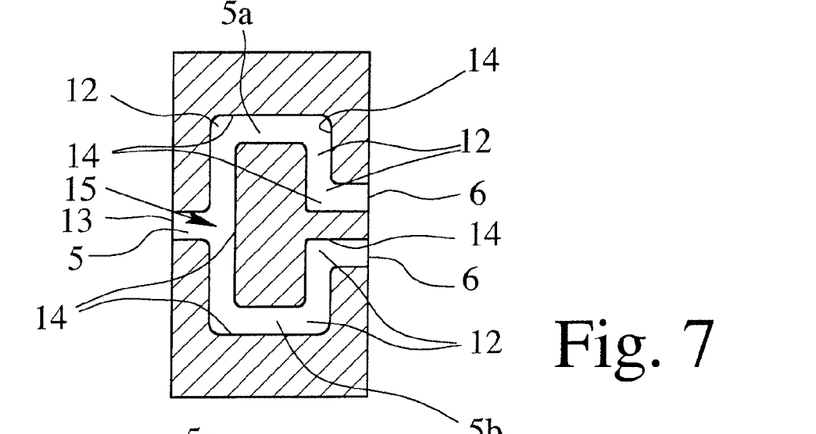
FIG. 7 is a schematic sectional view of a duct of a dispensing device according to another embodiment.
Figure 8:
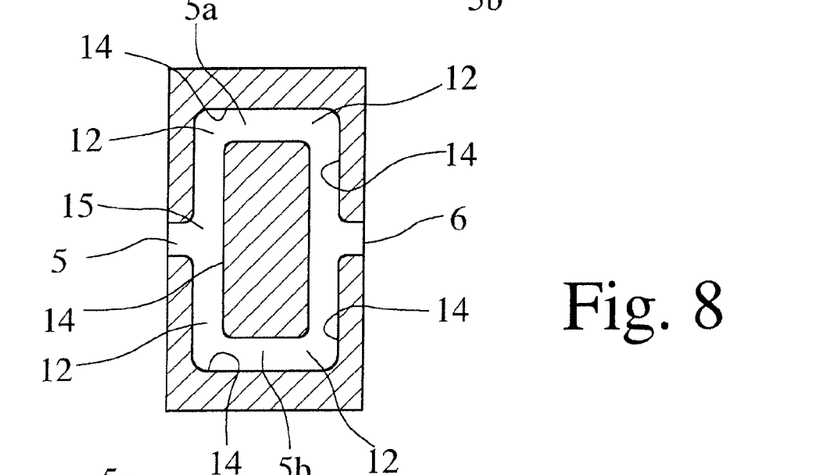
FIG. 8 is a schematic sectional view of a duct of a dispensing device according to another embodiment.
Figure 9:
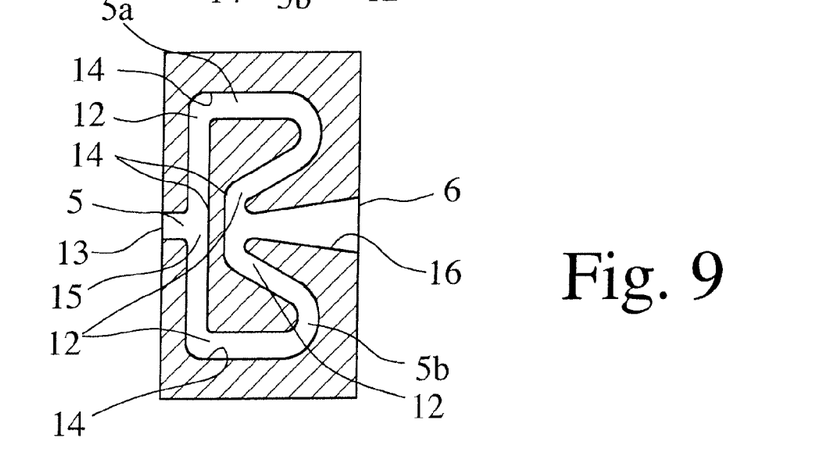
FIG. 9 is a schematic sectional view of a duct of a dispensing device according to yet another embodiment.
Figure 10:
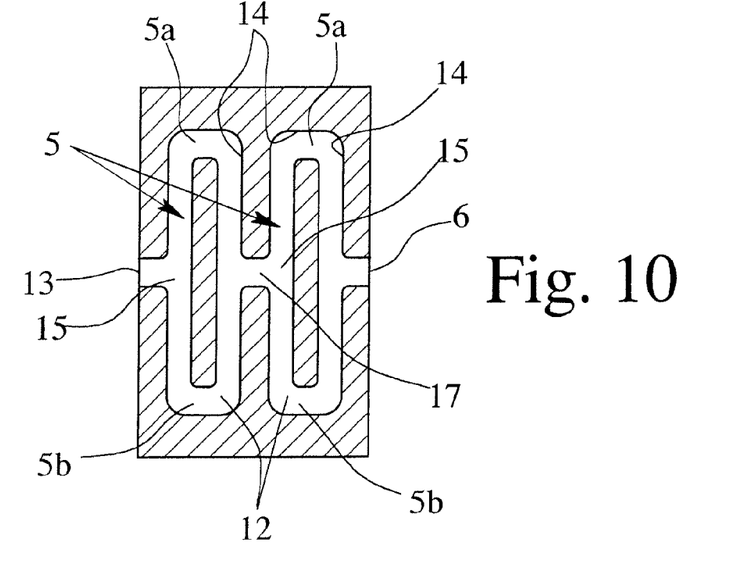
FIG. 10 is a schematic sectional view of a duct of a dispensing device according to another embodiment.

In the present invention, a cross section is considered to be flat when the ratio of the largest side d1 to the smallest side d2 of the cross section is at least 2.0. Preferably, the ratio is for 3 to 50 and in particular, about 5 to 70. It is pointed out that the cross sections shown in FIG. 6 are not in scale.

The largest side d1 is preferably, between 0.5 to 5 mm, in particular, 1 to 3 mm. Most preferably, the ratio of the largest side d1 to the (desired) fine particle size (mass mean diameter of the powder particles or drug particles of the spray 3) is less than 500, preferably, less than 300, in particular, about 30 to 300.

The smallest side d2 is preferably, between 0.05 to 0.5 mm, in particular, about 0.07 to 0.25 mm. Most preferably, the ratio of the smallest side d2 to the mass mean (desired) fine particle size (mass mean diameter of the powder particles/drug particles of the spray 3) is less than 50, preferably, less than 30, in particular, about 3 to 20.

The length of the duct 5 preferably, means the length with the flat cross section. Thus, the duct 5 can have a larger length, i.e., further portions with another cross sectional shape and/or with a larger cross sectional area so that the influence of these other portions is low on the mixture of gas and powder 2 in comparison to the portion of the duct 5 with the flat cross section. However, the cross sectional area and/or the shape of the flat cross section may vary over the length of the duct 5 (the portion with the flat cross section). Thus, it is possible that the cross sectional area of the duct 5 tapers from the inlet to the outlet or visa versa.

Most preferably, the duct 5 comprises at least one portion of flat cross section with constant cross section area, i.e., constant diameter and/or shape.

The length of the duct 5—i.e., the portion with flat cross section—may be in the range of 3 mm to 80 mm, in particular, 5 to 15 mm. Preferably, the duct length is adapted to the mean hydraulic diameter of the duct 5 such that the ratio of the length of the duct 5 to the mean hydraulic diameter is at least 5, in particular about 10, preferably, 20 to 60, or more, wherein the hydraulic diameter is defined as the ratio of four times cross-sectional area divided by the duct perimeter.

The diameter of the preferably, circular or cylindrical or conical chamber 10 depends on the volume of mass of the respective dose of powder 2. A single dose may have, e.g., 1 to 2 mg (pure drug without carrier) or 2 to 10 mg (blend of drug with carrier, in particular, lactose). In the first case, the range of the diameter is preferably, 1.5 to 2.5 mm. In the second case, the range of the diameter is preferably, between 2 and 5 mm. Preferably, the cross section of the duct 5 varies in a similar manner. For example, the smallest side d2 is about 0.07 to 0.1 mm in the first case and about 0.15 to 0.25 mm in the second case. The larger (inner) side d1 does not depend so strongly on the powder or particle size. Preferably, it is in the range of about 1 to 2 mm in the first case and 1 to 3 mm in the second case.

The mean hydraulic diameter of the duct 5 is preferably, less than 1 mm, in particular 0.1 mm to 0.6 mm.

Preferably, the duct 5 is molded and/or formed by a flat groove with a cover.

The dispensing device 1 or storage device 4 may comprise multiple ducts 5 for dispensing simultaneously a dose of powder 2, in particular, for increasing the total mass flow or output of dispensed powder 2 so that a desired dose can be discharged or dispensed in a sufficiently short time as desired and/or required.

Figure 14:
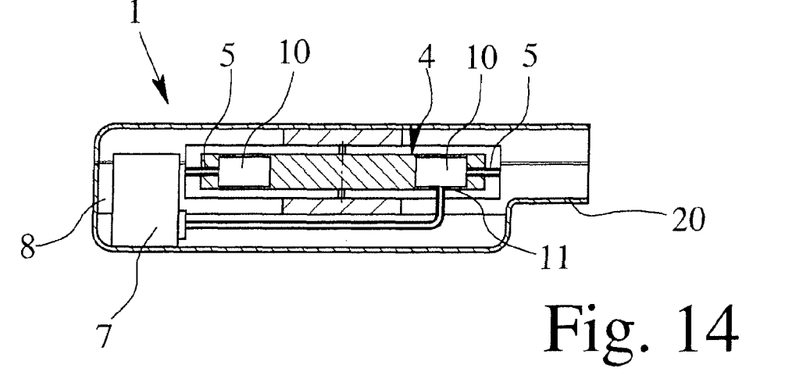
FIG. 14 is a schematic sectional view of a dispensing device according to another embodiment.

FIG. 14 shows another embodiment of the dispensing device 1 in a very schematic sectional view. In this embodiment, the storage device 4 is a, preferably, disc-shaped cartridge, container, blister or the like with multiple storage cavities. The storage device 4 can be rotated or indexed stepwise so that the powder 2 can be dispensed from the storage cavities 10 one after the other. In this embodiment, the gas may be supplied axially, and the mixture of gas and powder 2 may be dispensed radially, in particular, into the mouthpiece 20 for a user or patient (not shown). Preferably, the powder 2 is dispensed through at least one duct 5 and/or a outlet 6 directly into the mouthpiece 20. Most preferably, the duct 5/outlet 6 is located within the mouthpiece 20 and, in particular, set back with regard to the opening of the mouthpiece 20. This applies, preferably, also to the dispensing device 1 shown in FIGS. 1 & 2.

It is noted that the present invention, in particular, the dispensing device 1 and/or the storage device 4, can be used for dispensing one drug, a blend of drugs or at least two or three separate drugs. In the latter case, the separate drugs are stored in separate storage chambers 10 and, during the dispensing operation, the drugs are mixed either in a common mixing chamber or in their respective storage chambers 10 with the gas. Further, the separate drugs can be discharged through a common duct 5 or outlet 6 or through separate ducts 5 or outlets 6. In the latter case, the separate drugs will be mixed after leaving the separate ducts 5/outlets 6 or in the mouthpiece 20 or in any other suitable (additional) mixing chamber. It is also possible to mix the separate drugs by impinging powder jets of the separate drugs. For dispensing the separate drugs, it is possible to use a common gas supply or means for pressurizing gas such as the air pump 7 or separate gas supplies/means for providing pressurized gas. Further details of this embodiment can be found in commonly-owned, co-pending companion U.S. Ser. No. 11/576,853, which is hereby incorporated by reference.

It is noted that the different duct arrangements and/or different features of the duct arrangements and the different arrangements can be combined in any suitable manner.

In the following, two examples are described which show the effect of the present invention.

EXAMPLE 1

A blend of 90.0% by weight of lactose 200, of 9.7% by weight of fine lactose, and of 0.3% by weight of Tiotropium was used. The mean particle diameter of lactose 200 was about 45 μm, of fine lactose about 4 μm and of Tiotropium about 4 μm. About 5.5 mg of the blend was positioned as powder 2 in the storage and mixing chamber 10 which had a substantially cylindrical shape with a diameter of 3 mm and an axial length of 3 mm. 5 ml of compressed air was supplied via the gas inlet having an inlet orifice of 0.5 mm into the chamber 10 with a gauge pressure of about 100 kPa. The powder 2 was dispensed via duct 5 of substantially rectangular cross section having a smallest side of about 0.18 mm and a largest side of about 1.5 mm. The duct 5 divided into two duct sections 5a, 5b (in particular, as shown in FIG. 11), wherein each section had a substantially rectangular cross section with a smallest side of about 0.18 mm and the largest side of about 0.75 mm. The total length of the duct 5 including the sections 5a, 5b was about 8 mm. The result was that 100% of the metered mass, i.e., all powder 2 in chamber 10, was dispensed. Approximately 50% of both diameter mean and mass mean fine fraction was measured on an Anderson Cascade Impactor at both 30 and 60 l/min.

EXAMPLE 2

About 1.5 mg of Fenoterol with a mean particle diameter of 4 μm was positioned as powder 2 in the storage and mixing chamber 10 which had a substantially cylindrical shape with a diameter of 2 mm and an axial length of 2 mm. 5 ml of compressed air was supplied via the gas inlet having an inlet orifice of 0.5 mm into the chamber 10 with a gauge pressure of about 150 kPa. The powder 2 was dispensed via a duct 5 of substantially rectangular cross section having a smallest side of 0.075 mm and a largest side of 1.5 mm. The duct 5 divided into two duct sections 5a, 5b (in particular, as shown in FIG. 11), wherein each section had a substantially rectangular cross section with a smallest side of about 0.075 mm and the largest side of about 0.75 mm. The total length of the channel including the sections 5a, 5b was about 8 mm. The result was that 100% of the metered mass, i.e., all powder 2 in chamber 10, was dispensed. Approximately 45% of both diameter mean and mass mean fine fraction was measured on a Anderson Cascade Impactor at both 30 and 60 l/min.

The powder 2 or drug may contain any one of the following substances or any mixtures thereof. It might contain additional pharmacologically active substances or mixtures of substances, preferably, selected from those groups:

The below mentioned compounds may be used on their own or combined with other active substances for use in the device according to this invention. These include, in particular, betamimetics, anticholinergics, corticosteroids, PDE4-inhibitors, LTD4-antagonists, EGFR-inhibitors, dopaminagonists, antiallergic agents, PAF-antagonists und PI3-kinase inhibitors, but also combinations of two or three active substances, that is:

Betamimetics with corticosteroids, PDE4-inhibitors, EGFR-inhibitors or LTD4-antagonists, Anticholinergics with betamimetics, corticosteroids, PDE4-inhibitors, EGFR-inhibitors or LTD4-antagonists, Corticosteroids with PDE4-inhibitors, EGFR-inhibitors or LTD4-antagonists PDE4-inhibitors with EGFR-inhibtors or LTD4-antagonists EGFR-inhibtors with LTD4-antagonists.

Examples of preferred betamimetics which may be mentioned include Albuterole, Arformoterole, Bambuterole, Bitolterole, Broxaterole, Carbuterole, Clenbuterole, Fenoterole, Formoterole, Hexoprenaline, Ibuterole, Isoetharine, Isoprenaline, Levosalbutamole, Mabuterole, Meluadrine, Metaproterenole, Orciprenaline, Pirbuterole, Procaterole, Reproterole, Rimiterole, Ritodrine, Salmefamole, Salmeterole, Soterenole, Sulphonterole, Terbutaline, Tiaramide, Tolubuterole, Zinterole, CHF-1035, HOKU-81, KUL-1248 and 3-(4-{6-[2-Hydroxy-2-(4-hydroxy-3-hydroxymethyl-phenyl)-ethylamino]-hexyloxy}-butyl)-benzyl-sulfonamide 5-[2-(5,6-Diethyl-indan-2-ylamino)-1-hydroxy-ethyl]-8-hydroxy-1H-quinolin-2-one 4-Hydroxy-7-[2-{[2-{[3-(2-phenylethoxy)propyl] sulphonyl}ethyl]-amino}ethyl]-2(3H)-benzothiazolone 1-(2-Fluoro-4-hydroxyphenyl)-2-[4-(1-benzimidazolyl)-2-methyl-2-butylamino]ethanole 1-[3-(4-Methoxybenzyl-amino)-4-hydroxyphenyl]-2-[4-(1-benzimidazolyl)-2-methyl-2-butylamino]ethanole 1-[2H-5-hydroxy-3-oxo-4H-1,4-benzoxazin-8-yl]-2-[3-(4-N,N-dimethylaminophenyl)-2-methyl-2-propylamino]ethanole 1-[2H-5-hydroxy-3-oxo-4H-1,4-benzoxazin-8-yl]-2-[3-(4-methoxyphenyl)-2-methyl-2-propylamino]ethanole 1-[2H-5-hydroxy-3-oxo-4H-1,4-benzoxazin-8-yl]-2-[3-(4-n-butyloxyphenyl)-2-methyl-2-propylamino]ethanole 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-Hydroxy-8-(1-hydroxy-2-isopropylaminobutyl)-2H-1,4-benzoxazin-3-(4H)-one 1-(4-Amino-3-chloro-5-trifluormethylphenyl)-2-tert.-butylamino)ethanol 6-Hydroxy-8-{1-hydroxy-2-[2-(4-methoxy-phenyl)-1,1-dimethyl-ethylamino]-ethyl}-4H-benzo[1,4]oxazin-3-one 6-Hydroxy-8-{1-hydroxy-2-[2-(4-phenoxy-acetic acid ethylester)-1,1-dimethyl-ethylamino]-ethyl}-4H-benzo[1,4]oxazin-3-one 6-Hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-Dimethyl-2-(2,4,6-trimethylphenyl)-ethylamino]-1-hydroxy-ethyl}-6-hydroxy-4H-benzo[1,4]oxazin-3-one 6-Hydroxy-8-{1-hydroxy-2-[2-(4-hydroxy-phenyl)-1,1-dimethyl-ethylamino]-ethyl}-4H-benzo[1,4]oxazin-3-one 6-Hydroxy-8-{1-hydroxy-2-[2-(4-isopropyl-phenyl)-1,1-dimethyl-ethylamino]-ethyl}-4H-benzo[1,4]oxazin-3-one 8-{2-[2-(4-Ethyl-phenyl)-1,1-dimethyl-ethylamino]-1-hydroxy-ethyl}-6-hydroxy-4H-benzo[1,4]oxazin-3-one 8-{2-[2-(4-Ethoxy-phenyl)-1,1-dimethyl-ethylamino]-1-hydroxy-ethyl}-6-hydroxy-4H-benzo[1,4]oxazin-3-one 4-(4-{2-[2-Hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-Difluor-phenyl)-1,1-dimethyl-ethylamino]-1-hydroxy-ethyl}-6-hydroxy-4H-benzo[1,4]oxazin-3-on 1-(4-Ethoxy-carbonylamino-3-cyano-5-fluorophenyl)-2-(tert.-butylamino)ethanol 2-Hydroxy-5-(1-hydroxy-2-{2-[4-(2-hydroxy-2-phenyl-ethylamino)-phenyl]-ethylamino}-ethyl)-benzaldehyde N-[2-Hydroxy-5-(1-hydroxy-2-{2-[4-(2-hydroxy-2-phenyl-ethylamino)-phenyl]-ethylamino}-ethyl)-phenyl]-formamide 8-Hydroxy-5-(1-hydroxy-2-{2-[4-(6-methoxy-biphenyl-3-ylamino)-phenyl]-ethylamino}-ethyl)-1H-quinolin-2-one 8-Hydroxy-5-[1-hydroxy-2-(6-phenethylamino-hexylamino)-ethyl]-1H-quinolin-2-one 5-[2-(2-{4-[4-(2-Amino-2-methyl-propoxy)-phenylamino]-phenyl}-ethylamino)-1-hydroxy-ethyl]-8-hydroxy-1H-quinolin-2-one

[3-(4-{6-[2-Hydroxy-2-(4-hydroxy-3-hydroxymethyl-phenyl)-ethylamino]-hexyloxy}-butyl)-5-methyl-phenyl]-urea 4-(2-{6-[2-(2,6-Dichloro-benzyloxy)-ethoxy]-hexylamino}-1-hydroxy-ethyl)-2-hydroxymethyl-phenol 3-(4-{6-[2-Hydroxy-2-(4-hydroxy-3-hydroxymethyl-phenyl)-ethylamino]-hexyloxy}-butyl)-benzene-sulfonamide 3-(3-{7-[2-Hydroxy-2-(4-hydroxy-3-hydroxymethyl-phenyl)-ethylamino]-heptyloxy}-propyl)-benzene-sulfonamide 4-(2-{6-[4-(3-Cyclopentanesulfonyl-phenyl)-butoxy]-hexylamino}-1-hydroxy-ethyl)-2-hydroxymethyl-phenol N-Adamantan-2-yl-2-(3-{2-[2-hydroxy-2-(4-hydroxy-3-hydroxymethyl-phenyl)-ethylamino]-propyl}-phenyl)-acetamide optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred anticholinergics which may be mentioned include Tiotropium salts, preferred the bromide salt, Oxitropium salts, preferred the bromide salt, Flutropium salts, preferred the bromide salt, Ipratropium salts, preferred the bromide salt, Glycopyrronium salts, preferred the bromide salt, Trospium salts, preferred the chloride salt, Tolterodin. From the above mentioned salts the pharmacologically active part is the cation, possible anions are chloride, bromide, iodide, sulfate, phosphate, methansulfonate, nitrate, maleate, acetate, citrate, fumarate, tartrate, oxalate, succinate, benzoate oder p-toluenesulfonate. Furthermore 2,2-Diphenylpropion acid tropenolester-methobromide
2,2-Diphenylpropion acid scopinester-methobromide
2-Fluor-2,2-Diphenylacetic acid scopinester-methobromide
2-Fluor-2,2-Diphenylacetic acid tropenolester-methobromide
3,3',4,4'-Tetrafluorbenzil acid tropenolester-Methobromide
3,3',4,4'-Tetrafluorbenzil acid scopinester-Methobromide
4,4'-Difluorbenzil acid tropenolester-Methobromide
4,4'-Difluorbenzil acid scopinester-Methobromide
3,3'-Difluorbenzil acid tropenolester-Methobromide
3,3'-Difluorbenzil acid scopinester-Methobromide
9-Hydroxy-fluoren-9-carbon acid tropenolester-Methobromide
9-Fluor-fluoren-9-carbon acid tropenolester-Methobromide
9-Hydroxy-fluoren-9-carbon acid scopinester-Methobromide
9-Fluor-fluoren-9-carbon acid scopinester Methobromide
9-Methyl-fluoren-9-carbon acid tropenolesterMethobromide
9-Methyl-fluoren-9-carbon acid scopinesterMethobromide
Benzil acid cyclopropyltropinester-Methobromide
2,2-Diphenylpropion acid cyclopropyltropinester-Methobromide
9-Hydroxy-xanthen-9-carbon acid cyclopropyltropinesterMethobromide
9-Methyl-fluoren-9-carbon acid cyclopropyltropinester-Methobromide
9-Methyl-xanthen-9-carbon acid cyclopropyltropinester-Methobromide
9-Hydroxy-fluoren-9-carbon acid cyclopropyltropinester-Methobromide
4,4'-Difluorbenzil acid methylestercyclopropyltropinester-Methobromide
9-Hydroxy-xanthen-9-carbon acid tropenolester-Methobromide
9-Hydroxy-xanthen-9-carbon acid scopinester Methobromide
9-Methyl-xanthen-9-carbon acid tropenolester-Methobromide
9-Methyl-xanthen-9-carbon acid scopinesterMethobromide
9-Ethyl-xanthen-9-carbon acid tropenolester Methobromide
9-Difluormethyl-xanthen-9-carbon acid tropenolester-Methobromide
9-Hydroxymethyl-xanthen-9-carbon acid scopinester-Methobromide Examples of preferred corticosteroids which may be mentioned include Beclomethasone, Betamethasone, Budesonide, Butixocorte, Ciclesonide, Deflazacorte, Dexamethasone, Etiprednole, Flunisolide, Fluticasone, Loteprednole, Mometasone, Prednisolone, Prednisone, Rofleponide, Triamcinolone, RPR-106541, NS-126, ST-26 and 6,9-Difluoro-17-[(2-furanylcarbonyl)oxy]-11-hydroxy-16-methyl-3-oxo-androsta-1,4-dien-17-carbothion acid (S)-fluoromethylester 6,9-Difluoro-11-hydroxy-16-methyl-3-oxo-17-propionyloxy-androsta-1,4-dien-17-carbothion acid (S)-(2-oxo-tetrahydro-furan-3S-yl)ester, 6,9-difluoro-11-hydroxy-16-methyl-3-oxo-17-(2,2,3,3-tertamethylcyclo-propylcarbonyl)oxy-androsta-1,4-dien-17-carboxylic acid cyanomethyl ester optionally in racemic form, as enantiomers, diastereomeres or as pharmacologically acceptable salts, solvates or hydrates. Examples for preferred salts and derivatives are alkali salts, i.e., sodium or potassium salts, sulfobenzoates, phosphates, isonicotinates, acetates, dichloroacetates, propionates, dihydrogenphosphates, palmitates, pivalates or furoates.

Examples of preferred PDE4-inhibtors which may be mentioned include Enprofylline, Theophylline, Roflumilaste, Ariflo (Cilomilast), Tofimilaste, Pumafentrine, Lirimilaste, Arofylline, Atizorame, D-4418, Bay-198004, BY343, CP-325,366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and
- N-(3,5-Dichloro-1-oxo-pyridin-4-yl)-4-difluoromethoxy-3-cyclopropylmethoxy-benzamide
- (−)p-[(4aR*,10bS*)-9-Ethoxy-1,2,3,4,4a,10b-hexahydro-8-methoxy-2-methylbenzo[s][1,6]naphthyridin-6-yl]-N,N-diisopropylbenzamid
- (R)-(+)-1-(4-Bromobenzyl)-4-[(3-cyclopentyloxy)-4-methoxyphenyl]-2-pyrrolidon
- 3-(Cyclopentyloxy-4-methoxyphenyl)-1-(4-N'-[N-2-cyano-S-methyl-isothioureido]benzyl)-2-pyrrolidone
- cis[4-Cyano-4-(3-cyclopentyloxy-4-methoxyphenyl)cyclohexan-1-carbon acid]
- 2-carbomethoxy-4-cyano-4-(3-cyclopropylmethoxy-4-difluoromethoxy-phenyl)cyclohexan-1-one
- cis[4-Cyano-4-(3-cyclopropylmethoxy-4-difluoromethoxyphenyl)cyclohexan-1-ol]
- (R)-(+)-Ethyl[4-(3-cyclopentyloxy-4-methoxyphenyl)pyrrolidin-2-yliden]acetate
- (S)-(−)-Ethyl[4-(3-cyclopentyloxy-4-methoxyphenyl)pyrrolidin-2-yliden]acetate
- 9-Cyclopentyl-5,6-dihydro-7-ethyl-3-(2-thienyl)-9H-pyrazolo[3,4-c]-1,2,4-triazolo[4,3-a]pyridine
- 9-Cyclopentyl-5,6-dihydro-7-ethyl-3-(tert-butyl)-9H-pyrazolo[3,4-c]-1,2,4-triazolo[4,3-a]pyridine optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred LTD4-antagonists which may be mentioned include Montelukaste, Pranlukaste, Zafirlukaste, MCC-847 (ZD-3523), MN-001, MEN-91507 (LM-1507), VUF-5078, VUF-K-8707, L-733321 and
- 1-(((R)-(3-(2-(6,7-Difluoro-2-quinolinyl)ethenyl)phenyl)-3-(2-(2-hydroxy-2-propyl)phenyl)thio)methylcyclopropane-acetic acid,
- 1-(((1R)-3(3-(2-(2,3-Dichlorothieno[3,2-b]pyridin-5-yl)-(E)-ethenyl)phenyl)-3-(2-(1-hydroxy-1-methylethyl)phenyl)propyl)thio)methyl)cyclopropane acetic acid
- [2-[[2-(4-tert-Butyl-2-thiazolyl)-5-benzofuranyl]oxymethyl]phenyl]acetic acid optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate. Further examples for optionally preferred salts and derivatives are alkali salts, i.e., sodium or potassium salts, sulfobenzoates, phosphates, isonicotinates, acetates, propionates, dihydrogenphosphates, palmitates, pivalates or furoates.

Examples of preferred EGFR-inhibtors which may be mentioned include Cetuximabe, Trastuzumabe, ABX-EGF, Mab ICR-62 and
- 4-[(3-Chlor-4-fluorphenyl)amino]-6-{[4-(morpholin-4-yl)-1-oxo-2-buten-1-yl]-amino}-7-cyclopropylmethoxy-chinazoline
- 4-[(3-Chlor-4-fluorphenyl)amino]-6-{[4-(N,N-diethylamino)-1-oxo-2-buten-1-yl]-amino}-7-cyclopropylmethoxy-chinazoline
- 4-[(3-Chlor-4-fluorphenyl)amino]-6-{[4-(N,N-dimethylamino)-1-oxo-2-buten-1-yl]amino}-7-cyclopropylmethoxy-chinazoline
- 4-[(R)-(1-Phenyl-ethyl)amino]-6-{[4-(morpholin-4-yl)-1-oxo-2-buten-1-yl]amino}-7-cyclopentyloxy-chinazoline
- 4-[(3-Chlor-4-fluor-phenyl)amino]-6-{[4-((R)-6-methyl-2-oxo-morpholin-4-yl)-1-oxo-2-buten-1-yl]amino}-7-cyclopropylmethoxy-chinazoline
- 4-[(3-Chlor-4-fluor-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-chinazoline
- 4-[(3-Chlor-4-fluor-phenyl)amino]-6-{[4-((R)-2-methoxymethyl-6-oxo-morpholin-4-yl)-1-oxo-2-buten-1-yl]amino}-7-cyclopropylmethoxy-chinazoline
- 4-[(3-Chlor-4-fluor-phenyl)amino]-6-[2-((S)-6-methyl-2-oxo-morpholin-4-yl)-ethoxy]-7-methoxy-chinazoline
- 4-[(3-Chlor-4-fluorphenyl)amino]-6-({4-[N-(2-methoxyethyl)-N-methyl-amino]-1-oxo-2-buten-1-yl}amino)-7-cyclopropylmethoxy-chinazoline
- 4-[(3-Chlor-4-fluorphenyl)amino]-6-{[4-(N,N-dimethylamino)-1-oxo-2-buten-1-yl]amino}-7-cyclopentyloxy-chinazoline
- 4-[(R)-(1-Phenyl-ethyl)amino]-6-{[4-(N,N-bis-(2-methoxy-ethyl)-amino)-1-oxo-2-buten-1-yl]amino}-7-cyclopropylmethoxy-chinazoline
- 4-[(R)-(1-Phenyl-ethyl)amino]-6-({4-[N-(2-methoxyethyl)-N-ethyl-amino]-1-oxo-2-buten-1-yl}amino)-7-cyclopropylmethoxy-chinazoline
- 4-[(R)-(1-Phenyl-ethyl)amino]-6-({4-[N-(2-methoxyethyl)-N-methyl-amino]-1-oxo-2-buten-1-yl}amino)-7-cyclopropylmethoxy-chinazoline
- 4-[(R)-(1-Phenyl-ethyl)amino]-6-({4-[N-(tetrahydropyran-4-yl)-N-methyl-amino]-1-oxo-2-buten-1-yl}amino)-7-cyclopropylmethoxy-chinazoline
- 4-[(3-Chlor-4-fluorphenyl)amino]-6-{[4-(N,N-dimethylamino)-1-oxo-2-buten-1-yl]amino}-7-((R)-tetrahydrofuran-3-yloxy)-chinazoline
- 4-[(3-Chlor-4-fluorphenyl)amino]-6-{[4-(N,N-dimethylamino)-1-oxo-2-buten-1-yl]amino}-7-((S)-tetrahydrofuran-3-yloxy)-chinazoline
- 4-[(3-Chlor-4-fluorphenyl)amino]-6-({4-[N-(2-methoxyethyl)-N-methyl-amino]-1-oxo-2-buten-1-yl}amino)-7-cyclopentyloxy-chinazoline
- 4-[(3-Chlor-4-fluorphenyl)amino]-6-{[4-(N-cyclopropyl-N-methyl-amino)-1-oxo-2-buten-1-yl]amino}-7-cyclopentyloxy-chinazoline
- 4-[(3-Chlor-4-fluorphenyl)amino]-6-{[4-(N,N-dimethylamino)-1-oxo-2-buten-1-yl]amino}-7-[(R)-(tetrahydrofuran-2-yl)methoxy]-chinazoline
- 4-[(3-Chlor-4-fluorphenyl)amino]-6-{[4-(N,N-dimethylamino)-1-oxo-2-buten-1-yl]amino}-7-[(S)-(tetrahydrofuran-2-yl)methoxy]-chinazoline 4-[(3-Ethinyl-phenyl)amino]-6,7-bis-(2-methoxy-ethoxy)-chinazoline 4-[(3-Chlor-4-fluorphenyl)amino]-7-[3-(morpholin-4-yl)-propyloxy]-6-[(vinyl-carbonyl)amino]-chinazoline 4-[(R)-(1-Phenyl-ethyl)amino]-6-(4-hydroxy-phenyl)-7H-pyrrolo[2,3-d]pyrimidine 3-Cyano-4-[(3-chlor-4-fluorphenyl)amino]-6-{[4-(N,N-dimethylamino)-1-oxo-2-buten-1-yl]amino}-7-ethoxy-chinoline 4-{[3-Chlor-4-(3-fluor-benzyloxy)-phenyl]amino}-6-(5-{[(2-methansulfonyl-ethyl)amino]methyl}-furan-2-yl)chinazoline 4-[(R)-(1-Phenyl-ethyl)amino]-6-{[4-((R)-6-methyl-2-oxo-morpholin-4-yl)-1-oxo-2-buten-1-yl]amino}-7-methoxy-chinazoline 4-[(3-Chlor-4-fluorphenyl)amino]-6-{[4-(morpholin-4-yl)-1-oxo-2-buten-1-yl]-amino}-7-[(tetrahydrofuran-2-yl)methoxy]-chinazoline 4-[(3-Chlor-4-fluorphenyl)amino]-6-({4-[N,N-bis-(2-methoxy-ethyl)-amino]-1-oxo-2-buten-1-yl}amino)-7-[(tetrahydrofuran-2-yl)methoxy]-chinazoline 4-[(3-Ethinyl-phenyl)amino]-6-{[4-(5,5-dimethyl-2-oxo-morpholin-4-yl)-1-oxo-2-buten-1-yl]amino}-chinazoline 4-[(3-Chlor-4-fluor-phenyl)amino]-6-[2-(2,2-dimethyl-6-oxo-morpholin-4-yl)-ethoxy]-7-methoxy-chinazoline 4-[(3-Chlor-4-fluor-phenyl)amino]-6-[2-(2,2-dimethyl-6-oxo-morpholin-4-yl)-ethoxy]-7-[(R)-(tetrahydrofuran-2-yl)methoxy]-chinazoline 4-[(3-Chlor-4-fluor-phenyl)amino]-7-[2-(2,2-dimethyl-6-oxo-morpholin-4-yl)-ethoxy]-6-[(S)-(tetrahydrofuran-2-yl)methoxy]-chinazoline 4-[(3-Chlor-4-fluor-phenyl)amino]-6-{2-[4-(2-oxo-morpholin-4-yl)-piperidin-1-yl]-ethoxy}-7-methoxy-chinazoline 4-[(3-Chlor-4-fluor-phenyl)amino]-6-[1-(tert.-butyloxycarbonyl)-piperidin-4-yloxy]-7-methoxy-chinazoline 4-[(3-Chlor-4-fluor-phenyl)amino]-6-(trans-4-amino-cyclohexan-1-yloxy)-7-methoxy-chinazoline 4-[(3-Chlor-4-fluor-phenyl)amino]-6-(trans-4-methansulfonylamino-cyclohexan-1-yloxy)-7-methoxy-chinazoline 4-[(3-Chlor-4-fluor-phenyl)amino]-6-(tetrahydropyran-3-yloxy)-7-methoxy-chinazoline 4-[(3-Chlor-4-fluor-phenyl)amino]-6-(1-methyl-piperidin-4-yloxy)-7-methoxy-chinazoline 4-[(3-Chlor-4-fluor-phenyl)amino]-6-{1-[(morpholin-4-yl)carbonyl]-piperidin-4-yl-oxy}-7-methoxy-chinazoline 4-[(3-Chlor-4-fluor-phenyl)amino]-6-{1-[(methoxymethyl)carbonyl]-piperidin-4-yl-oxy}-7-methoxy-chinazoline 4-[(3-Chlor-4-fluor-phenyl)amino]-6-(piperidin-3-yloxy)-7-methoxy-chinazoline 4-[(3-Chlor-4-fluor-phenyl)amino]-6-[1-(2-acetylamino-ethyl)-piperidin-4-yloxy]-7-methoxy-chinazoline 4-[3-Chlor-4-fluor-phenyl)amino]-6-(tetrahydropyran-4-yloxy)-7-ethoxy-chinazoline 4-[(3-Chlor-4-fluor-phenyl)amino]-6-((S)-tetrahydrofuran-3-yloxy)-7-hydroxy-chinazoline 4-[(3-Chlor-4-fluor-phenyl)amino]-6-(tetrahydropyran-4-yloxy)-7-(2-methoxy-ethoxy)-chinazoline 4-[(3-Chlor-4-fluor-phenyl)amino]-6-{trans-4-[(dimethylamino)sulfonylamino]-cyclohexan-1-yloxy}-7-methoxy-chinazoline 4-[(3-Chlor-4-fluor-phenyl)amino]-6-{trans-4-[(morpholin-4-yl)carbonylamino]-cyclohexan-1-yloxy}-7-methoxy-chinazoline 4-[(3-Chlor-4-fluor-phenyl)amino]-6-{trans-4-[(morpholin-4-yl)sulfonylamino]-cyclohexan-1-yloxy}-7-methoxy-chinazoline 4-[(3-Chlor-4-fluor-phenyl)amino]-6-(tetrahydropyran-4-yloxy)-7-(2-acetylamino-ethoxy)-chinazoline 4-[(3-Chlor-4-fluor-phenyl)amino]-6-(tetrahydropyran-4-yloxy)-7-(2-methansulfonylamino-ethoxy)-chinazoline 4-[(3-Chlor-4-fluor-phenyl)amino]-6-{1-[(piperidin-1-yl)carbonyl]-piperidin-4-yloxy}-7-methoxy-chinazoline 4-[(3-Chlor-4-fluor-phenyl)amino]-6-(1-aminocarbonylmethyl-piperidin-4-yloxy)-7-methoxy-chinazoline 4-[(3-Chlor-4-fluor-phenyl)amino]-6-(cis-4-{N-[(tetrahydropyran-4-yl)carbonyl]-N-methyl-amino}-cyclohexan-1-yloxy)-7-methoxy-chinazoline 4-[(3-Chlor-4-fluor-phenyl)amino]-6-(cis-4-{N-[(morpholin-4-yl)carbonyl]-N-methyl-amino}-cyclohexan-1-yloxy)-7-methoxy-chinazoline 4-[(3-Chlor-4-fluor-phenyl)amino]-6-(cis-4-{N-[(morpholin-4-yl)sulfonyl]-N-methyl-amino}-cyclohexan-1-yloxy)-7-methoxy-chinazoline 4-[(3-Chlor-4-fluor-phenyl)amino]-6-(trans-4-ethansulfonylamino-cyclohexan-1-yloxy)-7-methoxy-chinazoline 4-[(3-Chlor-4-fluor-phenyl)amino]-6-(1-methansulfonyl-piperidin-4-yloxy)-7-ethoxy-chinazoline 4-[(3-Chlor-4-fluor-phenyl)amino]-6-(1-methansulfonyl-piperidin-4-yloxy)-7-(2-methoxy-ethoxy)-chinazoline 4-[(3-Chlor-4-fluor-phenyl)amino]-6-[1-(2-methoxyacetyl)-piperidin-4-yloxy]-7-(2-methoxy-ethoxy)-chinazoline 4-[(3-Chlor-4-fluor-phenyl)amino]-6-(cis-4-acetylamino-cyclohexan-1-yloxy)-7-methoxy-chinazoline 4-[(3-Ethinyl-phenyl)amino]-6-[1-(tert.-butyloxycarbonyl)-piperidin-4-yloxy]-7-methoxy-chinazoline 4-[(3-Ethinyl-phenyl)amino]-6-(tetrahydropyran-4-yloxy]-7-methoxy-chinazoline 4-[(3-Chlor-4-fluor-phenyl)amino]-6-(cis-4-{N-[(piperidin-1-yl)carbonyl]-N-methyl-amino}-cyclohexan-1-yloxy)-7-methoxy-chinazoline 4-[(3-Chlor-4-fluor-phenyl)amino]-6-(cis-4-{N-[(4-methyl-piperazin-1-yl)carbonyl]-N-methyl-amino}-cyclohexan-1-yloxy)-7-methoxy-chinazoline 4-[(3-Chlor-4-fluor-phenyl)amino]-6-{cis-4-[(morpholin-4-yl)carbonylamino]-cyclohexan-1-yloxy}-7-methoxy-chinazoline 4-[(3-Chlor-4-fluor-phenyl)amino]-6-{1-[2-(2-oxopyrrolidin-1-yl)ethyl]-piperidin-4-yloxy}-7-methoxy-chinazoline 4-[(3-Chlor-4-fluor-phenyl)amino]-6-{1-[(morpholin-4-yl)carbonyl]-piperidin-4-yloxy}-7-(2-methoxy-ethoxy)-chinazoline 4-[(3-Ethinyl-phenyl)amino]-6-(1-acetyl-piperidin-4-yloxy)-7-methoxy-chinazoline 4-[(3-Ethinyl-phenyl)amino]-6-(1-methyl-piperidin-4-yloxy)-7-methoxy-chinazoline 4-[(3-Ethinyl-phenyl)amino]-6-(1-methansulfonyl-piperidin-4-yloxy)-7-methoxy-chinazoline 4-[(3-Chlor-4-fluor-phenyl)amino]-6-(1-methyl-piperidin-4-yloxy)-7(2-methoxy-ethoxy)-chinazoline 4-[(3-Chlor-4-fluor-phenyl)amino]-6-(1-isopropyloxycarbonyl-piperidin-4-yloxy)-7-methoxy-chinazoline 4-[(3-Chlor-4-fluor-phenyl)amino]-6-(cis-4-methylamino-cyclohexan-1-yloxy)-7-methoxy-chinazoline 4-[(3-Chlor-4-fluor-phenyl)amino]-6-{cis-4-[N-(2-methoxy-acetyl)-N-methyl-amino]-cyclohexan-1-yloxy}-7-methoxy-chinazoline 4-[(3-Ethinyl-phenyl)amino]-6-(piperidin-4-yloxy)-7-methoxy-chinazoline 4-[(3-Ethinyl-phenyl)amino]-6-[1-(2-methoxy-acetyl)-piperidin-4-yloxy]-7-methoxy-chinazoline 4-[(3-Ethinyl-phenyl)amino]-6-{1-[(morpholin-4-yl)carbonyl]-piperidin-4-yloxy}-7-methoxy-chinazoline 4-[(3-Chlor-4-fluor-phenyl)amino]-6-{1-[(cis-2,6-dimethyl-morpholin-4-yl)carbonyl]-piperidin-4-yloxy}-7-methoxy-chinazoline 4-[(3-Chlor-4-fluor-phenyl)amino]-6-{1-[(2-methyl-morpholin-4-yl)carbonyl]-piperidin-4-yloxy}-7-methoxy-chinazoline 4-[(3-Chlor-4-fluor-phenyl)amino]-6-{1-[(S,S)-(2-oxa-5-aza-bicyclo[2.2.1]hept-5-yl)carbonyl]-piperidin-4-yloxy}-7-methoxy-chinazoline 4-[(3-Chlor-4-fluor-phenyl)amino]-6-{1-[(N-methyl-N-2-methoxyethyl-amino)carbonyl]-piperidin-4-yloxy}-7-methoxy-chinazoline 4-[(3-Chlor-4-fluor-phenyl)amino]-6-(1-ethyl-piperidin-4-yloxy)-7-methoxy-chinazoline 4-[(3-Chlor-4-fluor-phenyl)amino]-6-{1-[(2-methoxy-ethyl)carbonyl]-piperidin-4-yloxy}-7-methoxy-chinazoline 4-[(3-Chlor-4-fluor-phenyl)amino]-6-{1-[(3-methoxypropyl-amino)-carbonyl]-piperidin-4-yloxy}-7-methoxy-chinazoline 4-[(3-Chlor-4-fluor-phenyl)amino]-6-[cis-4-(N-methansulfonyl-N-methyl-amino)-cyclohexan-1-yloxy]-7-methoxy-chinazoline 4-[(3-Chlor-4-fluor-phenyl)amino]-6-[cis-4-(N-acetyl-N-methyl-amino)-cyclohexan-1-yloxy]-7-methoxy-chinazoline 4-[(3-Chlor-4-fluor-phenyl)amino]-6-(trans-4-methylamino-cyclohexan-1-yloxy)-7-methoxy-chinazoline 4-[(3-Chlor-4-fluor-phenyl)amino]-6-[trans-4-(N-methansulfonyl-N-methyl-amino)-cyclohexan-1-yloxy]-7-methoxy-chinazoline 4-[(3-Chlor-4-fluor-phenyl)amino]-6-(trans-4-dimethylamino-cyclohexan-1-yloxy)-7-methoxy-chinazoline 4-[(3-Chlor-4-fluor-phenyl)amino]-6-(trans-4-{N-[(morpholin-4-yl)carbonyl]-N-methyl-amino}-cyclohexan-1-yloxy)-7-methoxy-chinazoline 4-[(3-Chlor-4-fluor-phenyl)amino]-6-[2-(2,2-dimethyl-6-oxo-morpholin-4-yl)-ethoxy]-7-[(S)-(tetrahydrofuran-2-yl)methoxy]-chinazoline 4-[(3-Chlor-4-fluor-phenyl)amino]-6-(1-methansulfonyl-piperidin-4-yloxy)-7-methoxy-chinazoline 4-[(3-Chlor-4-fluor-phenyl)amino]-6-(1-cyano-piperidin-4-yloxy)-7-methoxy-chinazoline optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred dopamin antagonists which may be mentioned include Bromocriptine, Cabergoline, Alpha-Dihydroergocryptine, Lisuride, Pergolide, Pramipexole, Roxindole, Ropinirole, Talipexole, Terguride and Viozane, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred antiallergic agents which may be mentioned include Epinastine, Cetirizine, Azelastine, Fexofenadine, Levocabastine, Loratadine, Mizolastine, Ketotifene, Emedastine, Dimetindene, Clemastine, Bamipine, Cexchlorpheniramine, Pheniramine, Doxylamine, Chlorphenoxamine, Dimenhydrinate, Diphenhydramine, Promethazine, Ebastine, Desloratidine and Meclozine, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Moreover, inhalable macromolecules can be used as pharmacologically active substances, as disclosed in European Patent Application EP 1 003 478 A1 or Canadian Patent Application CA 2297174 A1.

Moreover, the compound could be from the group of derivates of ergotalcaloids, triptane, CGRP-antagonists, phosphodiesterase-V-inhibitores, optionally, in the form of the racemates, the enantiomers, the diastereomers and optionally the pharmacologically acceptable acid addition salts and the hydrates thereof.

As derivates of alkaloides: dihydroergotamine, ergotamine.

What is claimed is:

1. Dispensing device for dispensing powder as a spray including fine powder particles, the dispensing device comprising:

at least one powder storage chamber, and at least one duct through which the powder is dispensable from the at least one powder storage chamber by gas pressure for de-agglomerating the powder, wherein the at least one duct is meander or zig-zag shaped along its length while maintaining an essentially constant diameter so that the powder is at least one of impacted on to and sheared by a solid surface for de-agglomeration of the powder.
    2. Dispensing device according to claim 1, wherein the at least one duct has multiple solid surfaces or surface portions with which the powder is at least one of impacted and sheared by for powder de-agglomeration.

3. Dispensing device according to claim 1, wherein the duct is angled alternately in opposite directions.

4. Dispensing device according to claim 1, wherein the duct is a capillary.

5. Dispensing device according to claim 1, wherein the duct directly exits into a mouthpiece of the dispensing device.

6. Dispensing device according to claim 1, wherein the duct has a flat cross section, wherein a ratio of the largest side to the smallest side of the flat cross section is at least 2.0.

7. Dispensing device according to claim 6, wherein the largest side is between 0.5 to 5 mm and wherein the flat cross section is substantially oval or rectangular.

8. Dispensing device according to claim 1, wherein the dispensing device comprises means for providing pressurized gas for at least one of forcing the powder through the duct and dispensing the powder.

9. Dispensing device according to claim 1, wherein the dispensing device comprises an air pump as means for providing pressurized gas, wherein the air pump is manually operated.

10. Dispensing device according to claim 1, wherein the storage chamber is in a replaceable storage device containing at least a single dose of powder is, so that the doses are dispensable subsequently.

11. Dispensing device according to claim 10, wherein the storage device is constructed such that each dose of powder is dispensed through a separate duct or outlet.

12. Dispensing device according to claim 10, wherein the storage device is a cartridge, blister, capsule or container.

13. Dispensing device according to claim 1, wherein the dispensing device comprises multiple ducts for dispensing simultaneously a dose of powder for increasing the total mass flow of dispensed powder.

14. Dispensing device according to claim 1, wherein a separate or unused duct is provided for dispensing each dose of powder.

15. Dispensing device according to claim 1, wherein a diffuser is provided for slowing down the propagation velocity of the spray.

16. Dispensing device according to claim 1, wherein a powder jet impinging means for impinging at least two powder jets is provided to at least one of further de-agglomerate the powder, slow down the propagation velocity of the spray and mix separate powders.

17. Dispensing device according to claim 1, wherein the device is adapted for use with a powder having a mean powder particle size of 2 to 7 μm when the powder is a pure drug or a blend of drugs, a mean powder particle size of 20 to 300 μm when the powder is a blend of a carrier with at least one drug.

18. Dispensing device according to claim 1, wherein the dispensing device is constructed as a dry powder inhaler.

19. Dispensing device according to claim 1, wherein the duct and storage chamber for the powder are formed of a one-piece construction.

* * * * *